US012584096B2

(12) United States Patent
Bianchi et al.

(10) Patent No.: US 12,584,096 B2
(45) Date of Patent: Mar. 24, 2026

(54) OLEAGINOUS YEAST STRAIN AND USE THEREOF FOR THE PRODUCTION OF LIPIDS

(71) Applicant: ENI S.P.A., Rome (IT)

(72) Inventors: Daniele Bianchi, Novara (IT); Daniela Cucchetti, Novara (IT); Concetta Compagno, Spino d'Adda (IT); Silvia Donzella, Salerno (IT)

(73) Assignee: ENI S.P.A., Rome (IT)

( * ) Notice: Subject to any disclaimer, the term of this patent is extended or adjusted under 35 U.S.C. 154(b) by 365 days.

(21) Appl. No.: 18/022,898

(22) PCT Filed: Aug. 24, 2021

(86) PCT No.: PCT/IB2021/057746
§ 371 (c)(1),
(2) Date: Feb. 23, 2023

(87) PCT Pub. No.: WO2022/043868
PCT Pub. Date: Mar. 3, 2022

(65) Prior Publication Data
US 2023/0303962 A1     Sep. 28, 2023

(30) Foreign Application Priority Data
Aug. 26, 2020     (IT) ........................ 102020000020458

(51) Int. Cl.
| | |
|---|---|
| C12N 1/16 | (2006.01) |
| C12N 1/165 | (2026.01) |
| C12P 7/6463 | (2022.01) |
| C12R 1/645 | (2006.01) |

(52) U.S. Cl.
CPC ............ C12N 1/165 (2021.05); C12P 7/6463 (2013.01); C12R 2001/645 (2021.05)

(58) Field of Classification Search
None
See application file for complete search history.

(56) References Cited

FOREIGN PATENT DOCUMENTS

| | | |
|---|---|---|
| EP | 1728844 A1 | 12/2006 |
| WO | 2014102254 A1 | 7/2014 |
| WO | 2019016703 A1 | 1/2019 |

OTHER PUBLICATIONS

Capusoni, C. et al., Characterization of lipid accumulation and lipidome analysis in the oleaginous yeasts *Rhodosporidium azoricum* and *Trichosporon oleaginosus*, Bioresource Technology 238 (2017) 281-289.
Choudhary, J. et al. "Thermotolerant fermenting yeasts for simultaneous saccharification fermentation of lignocellulosic biomass", EJB Electronic Journal of Biotechnology, vol. 21, May 1, 2016, pp. 82-92.

Coradetti, S. et al., "Functional genomics of lipid metabolism in the oleaginous yeast *Rhodosporidium toruloides*", (2018), eLife 2018; 7:e32110, 55 pages.
Ewing, B. et al., "Base-Calling of Automated Sequencer Traces Using Phred. I. Accuracy Assessment", Genome Research (1998), vol. 8(3), p. 175-185.
Folch, J. et al., "A Simple Method for the Isolation and Purification of Total Lipides From Animal Tissues" The Journal of Biological Chemistry, vol. 226, p. 497-509, Aug. 23, 23, 1956.
Galafassi, S. et al., "Lipid production for second generation biodiesel by the oleaginous yeast *Rhodotorula graminis*" Bioresource Technology (2012), vol. 111, pp. 398-403.
Grimminger-Marquardt, V. et al., "Review Structure and Function of the Molecular Chaperone Hsp104 from Yeast", (2009) Biopolymers, vol. 93, Issue 3, p. 252-276.
Hara, A. et al., "Lipid Extraction of Tissues with a Low-Toxicity Solvent", Analytical Biochemistry, vol. 90, p. 420-426 (1978).
Howard, M. et al., "Functional analysis of proposed substratebinding residues of Hsp104", Plos One, https://doi.org/10.1371/journal.pone.0230198 Mar. 10, 2020, 11 pages.
International Search Report for International Application No. PCT/IB2021/057746, International Filing Date Aug. 24, 2021, Date of Mailing Dec. 10, 2021, 5 pages.
Jarolim, S. et al., "Saccharomyces cerevisiae Genes Involved in Survival of Heat Shock", (2013) G3 (Bethesda), 9; 3(12), p. 2321-2333.
Larimer, F.W. et al. "The REV1 Gene of *Saccharomyces cerevisiae*: Isolation, Sequence, and Functional Analysis", (1988) Journal of bacteriology, vol. 171, No. 1, p. 230-237.
Lindquist, S. et al., "The Heat-Shock Proteins" Annual Review of Genetics, 1998, vol. 22, p. 631-677.
Nogue, V. et al., "Integrated diesel production from lignocellulosic sugars via oleaginous yeast", Green Chemistry, 20 (2018), pp. 4349-4365.
Nouri, H. et al., "Xylan-hydrolyzing thermotolerant Candida tropicalis HNMA-1 for bioethanol production from sugarcane bagasse hydrolysate", Anals of Microbiology, Distam, Mi Lan, IT, vol. 67, No. 9, Aug. 7, 2017 pp. 633-641.
Parsell, D. et al., "Protein disaggregation mediated by heat-shock protein Hsp104", Letters to Nature 372 (1994) 475-478.
Richter, K. et al., "The Heat Shock Response: Life on the Verge of Deat", Molecular Cell Review, 2010, vol. 40, Issue 2, p. 253-266.
Spanguolo, M. et al., "Oleaginous yeast for biofuel and oleochemical production", Currebt Opinion Biotechnoloy, Mar. 12, 2019; 57: 73-81. doi: 10.1016/j.copbio.2019.02.011.

(Continued)

*Primary Examiner* — Richard G Hutson
(74) *Attorney, Agent, or Firm* — CANTOR COLBURN LLP

(57) ABSTRACT

An oleaginous yeast strain of the species *Trichosporon oleaginosus*, deposited on May 28, 2020 at Leibniz-Institut DSMZ, deposit number DSM 33530 can be used in the production of lipids by fermentation and was obtained by mutagenesis and subsequent selection from the oleaginous yeast strain of the species *Trichosporon oleaginosus* DSM 32508. The strain DSM 33530 is characterized by high thermotolerance, such as to allow the fermentation temperature to be increased compared to conventional processes and still guarantee the vital functions of the microorganism during fermentation itself.

9 Claims, 5 Drawing Sheets

(56) References Cited

OTHER PUBLICATIONS

Treco, D. et al., "Growth and Manipulation of Yeast" Current Protocols in Molecular Biology 13.2.1-13.2.12, Apr. 2008, 12 pages.

Vasconcelos, B. et al., "Oleaginous yeasts for sustainable lipid production—from biodiesel to surf boards, a wide range of "green" applications" Applied Microbiology and Biotechnologyhttps://doi. org/10.1007/s00253-019-09742-x, Mar. 25, 2019, 17 pages.

Written Opinion for International Application No. PCT/IB2021/ 057746, International Filing Date Aug. 24, 2021, Date of Mailing Dec. 10, 2021, 5 pages.

TABLE 1

| Annotation | Scaffold | Position | Type | Length | Parental | Mutant | Mutated amino acid |
|---|---|---|---|---|---|---|---|
| fhl1 - Fork-Head Like protein | scaffold1026_size4668 mapping | 4620 | SNV | 1 | A | G | Gln1480Arg |
| | scaffold1026_size4668 mapping | 4622 | SNV | 1 | T | C | Ser1481Pro |
| | scaffold1026_size4668 mapping | 4627 | Insertion | 1 | . | A | His1483fs |
| ARG5.6 - Acetylglutamate kinase | scaffold1055_size8174 mapping | 3840 | Deletion | 3 | TCT | . | |
| acyP - Acylphosphatase | scaffold1193_size3301 mapping | 38 | SNV | 1 | A | G | |
| | scaffold1193_size3301 mapping | 44 | SNV | 1 | T | G | |
| snx12 - Sorting NeXin | scaffold11_size64597 mapping | 36341 | Deletion | 11 | GTC | . | Ser581fs |
| bimA - Intracellular motility protein A | scaffold1280_size3283 mapping | 2663 | Deletion | 1 | AgT | . | Ala754Gly |
| uba3 - UBiquitin-like protein | scaffold128_size30502 mapping | 29951 | SNV | 1 | C | C | Ala14Pro |
| MET3 - METhionine requiring | scaffold141_size36158 mapping | 41 | SNV | 1 | G | C | Ser15Ala |
| | scaffold141_size36158 mapping | 44 | SNV | 1 | T | G | Leu16fs |
| | scaffold141_size36158 mapping | 47 | Insertion | 1 | . | T | |
| GPA2 - G Protein Alpha subunit | scaffold1466_size2058 mapping | 1381 | Deletion | 5 | GGTGG | . | Cys178fs |
| DOCK4 - dedicator of cytokinesis protein 4 | scaffold167_size27024 mapping | 807 | Deletion | 1 | T | . | Arg1998Gln |
| cut6 - acetyl-CoA carboxylase | scaffold168_size26199 mapping | 19242 | SNV | 1 | CoG | ToA | |
| Wdr7 - WD repeat containing protein 7 | scaffold330_size18768 mapping | 13106 | SNV | 1 | C | T | Asn10fs |
| nrf1_1 - Nuclear respiratory factor 1 | scaffold371_size16180 mapping | 12792 | Insertion | 1 | . | C | Gly189Ser |
| HNM1_5 - Hyper-resistance to Nitrogen Mustard | scaffold373_size16052 mapping | 3781 | MNV | 2 | GG | AA | |
| tea1 - Ty Enhancer Activator | scaffold375_size1663 mapping | 1607 | SNV | 1 | C | T | Asn13His |
| hsp104 - Heat Shock Protein 104 | scaffold376_size20804 mapping | 38 | SNV | 1 | A | C | Pro14Arg |
| xlnD_3 - Xylan 1,4-beta-xylosidase | scaffold282_size17155 mapping | 42 | SNV | 1 | C | G | |
| ARG2 - arginase 2 | scaffold38_size49100 mapping | 50 | Deletion | 1 | C | . | Pro7fs |
| gcn1 - General Control Nonderepressible | scaffold446_size13602 mapping | 47 | Deletion | 1 | C | . | |
| HIS3_1 - HIStidine | scaffold588_size10669 mapping | 51 | SNV | 1 | G | C | Phe332Tyr |
| RFT1 - Requiring FiFty-Three | scaffold602_size10404 mapping | 8440 | SNV | 1 | T | A | |
| HSE1_1 - resembles Hbp, Stam and East | scaffold663_size40813 mapping | 15762 | SNV | 1 | ToA | GoC | |
| isA1 - Iron Sulfur Assembly | scaffold788_size10959 mapping | 4283 | SNV | 1 | G | C | |
| ADK_2 - Adenylate kinase | scaffold818_size6833 mapping | 6782 | SNV | 1 | T | G | |
| KGD1 - alpha-KetoGlutarate Dehydrogenase | scaffold878_size181 mapping | 4005 | SNV | 1 | T | C | Phe113Leu |
| | scaffold878_size181 mapping | 4008 | SNV | 1 | T | C | Phe1591Leu |
| REV1 - deoxycytidyl transferase | scaffold887_size634 mapping | 5217 | SNV | 1 | C | T | Ser1097Phe |

TABLE 2

| Annotation | Scaffold | Position | Type | Length | Parental | Mutant | Mutated amino acid |
|---|---|---|---|---|---|---|---|
| DRG2 - Developmentally-regulated GTP-binding protein 2 | scaffold102_size34202 mapping | 17507 | SNV | 1 | C | T | Ser24Leu |
| CYC1 - Cytochrome C | scaffold1035_size4543 mapping | 4206 | SNV | 1 | T | A | Gln102Leu |
| RPL7 - Ribosomal-Like Protein | scaffold1084_size4122 mapping | 2652 | SNV | 1 | T | C | Ser35Pro |
| oca2 - Oxidant-induced Cell cycle Arrest | scaffold1087_size4080 mapping | 436 | SNV | 1 | T | C | Ser35Pro |
| txl1 - Thioredoxin-like protein 1 | scaffold1142_size3681 mapping | 1794 | SNV | 1 | G | A | |
| FMM1 - FMN biosynthesis | scaffold115_size32555 mapping | 20701 | SNV | 1 | T | C | Lys199Arg |
| pkiA - cAMP-dependent protein kinase inhibitor | scaffold116_size41062 mapping | 1471 | SNV | 1 | C | T | |
| uap3 - UDP-N-acetylglucosamine pyrophosphorylase | scaffold125_size31167 mapping | 13934 | SNV | 1 | T | A | Phe178Tyr |
| CAT2 - Carnitine Acetyltransferase | scaffold1282_size2620 mapping | 1693 | SNV | 1 | C | T | Asp68Asn |
| NUP205 - Nucleus Pore | scaffold4146_size28370 mapping | 18457 | SNV | 1 | T | A | |
| APX3 - L-ascorbate peroxidase 3 | scaffold153_size39380 mapping | 10248 | SNV | 1 | C | T | Gly541Asp |
| NST3_1 - Homolog of SIR Two (SIR2) | scaffold159_size34484 mapping | 1500 | SNV | 1 | C | T | |
| RIM13 - Regulator of IME2 | scaffold174_size27160 mapping | 10110 | Deletion | 1 | G | - | Gly94fs |
| GSG2 - Germ cell-specific gene 2 | scaffold195_size24175 mapping | 6150 | SNV | 1 | G | T | Val81Leu |
| FZR2 - fizzy-related 2 | scaffold209_size42628 mapping | 30656 | SNV | 1 | G | A | Ala357Thr |
| | scaffold209_size42628 mapping | 30658 | SNV | 1 | G | A | Val261Met |
| ADC2 - ADEnine requiring | scaffold222_size22404 mapping | 5248 | SNV | 1 | A | G | |
| CPR1 - Cyclosporin A-sensitive Proline Rotamase | scaffold4235_size213983 mapping | 20943 | SNV | 1 | C | T | Ser24Leu |
| KGD2 - alpha-Ketoglutarate Dehydrogenase | scaffold23_size4972 mapping | 37521 | SNV | 1 | C | T | |
| VMS1 - VCP/Cdc48-associated Mitochondrial Stress-responsive | scaffold261_size21074 mapping | 8138 | Deletion | 1 | C | - | Phe80fs |
| RKI1 - Ribose-5-phosphate Ketol-isomerase | scaffold262_size20518 mapping | 9330 | MNV | 2 | AG | GA | |
| RPO41 - RNA Polymerase | scaffold274_size20098 mapping | 8523 | MNV | 2 | CC | TT | |
| MNS1 - Alpha-1,2-mannosidase | scaffold2_size104624 mapping | 93223 | SNV | 1 | G | T | Asp281Tyr |
| sks2 - Suppressor Kinase of SNF3 | scaffold315_size17934 mapping | 5796 | Deletion | 1 | C | - | |
| sgt2 - Glutamine-rich cytoplasmic cochaperone | scaffold315_size17934 mapping | 15883 | SNV | 1 | T | C | |
| MEF1 - Mitochondrial Elongation Factor | scaffold320_size17801 mapping | 14834 | SNV | 1 | C | A | Phe586Leu |
| FRE3 - Ferric Reductase | scaffold32_size151576 mapping | 22376 | SNV | 1 | T | C | |
| COX18 - Cytochrome c Oxidase | scaffold340_size17542 mapping | 3296 | SNV | 1 | G | A | |
| RAD5_1 - RADiation sensitive | scaffold350_size25995 mapping | 8720 | SNV | 1 | T | G | Gly1194Val |
| ABCD2_1 - ATP-binding cassette sub-family C | scaffold350_size25995 mapping | 21373 | SNV | 1 | T | G | His665Gln |

Fig. 2

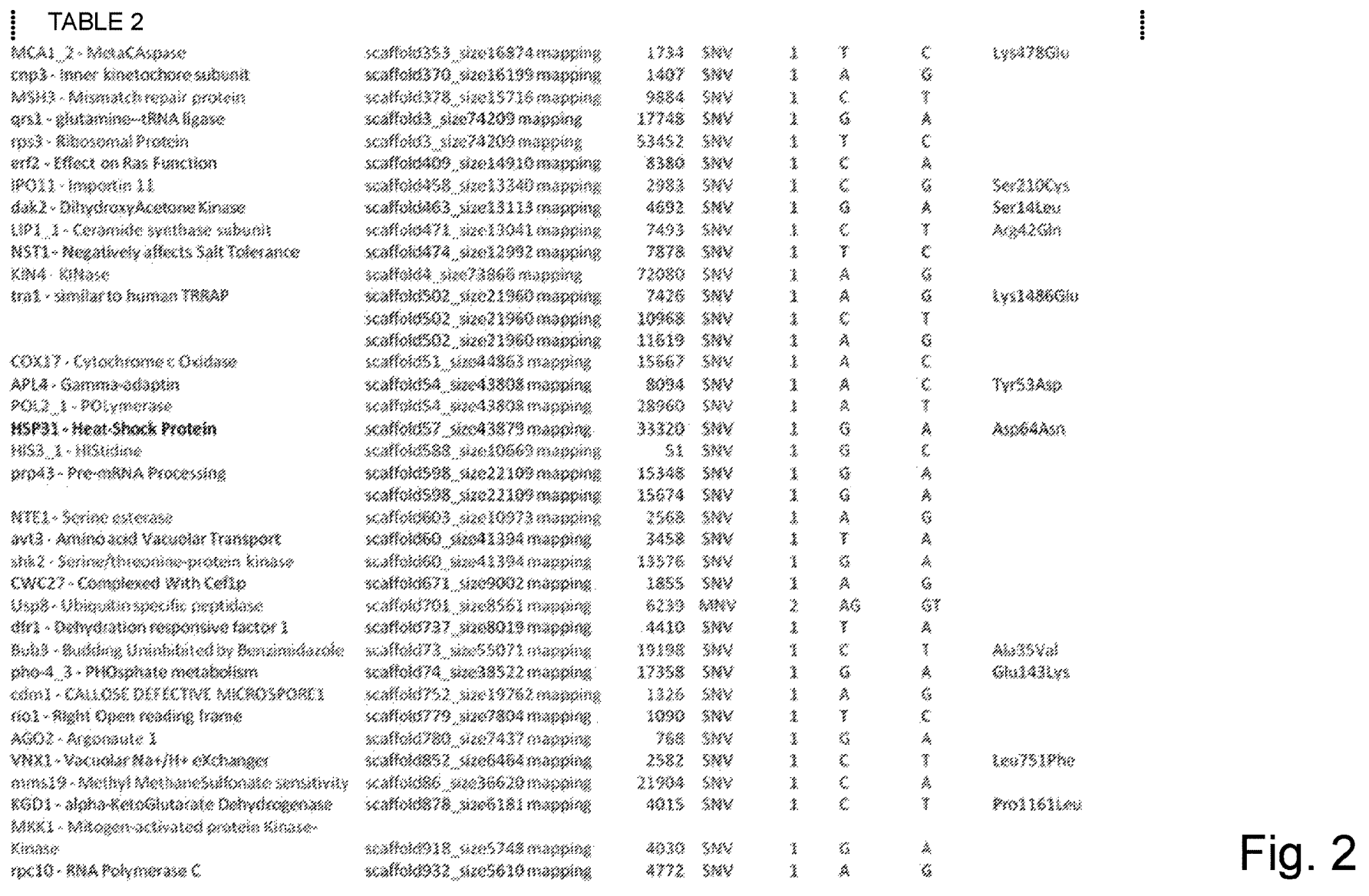

TABLE 2

| Gene | Scaffold | Position | Type | Count | Ref | Alt | AA change |
|---|---|---|---|---|---|---|---|
| MCA1_2 - MetaCaspase | scaffold353_size16874 er.mapping | 1734 | SNV | 1 | T | C | Lys478Glu |
| cmp3 - inner kinetochore subunit | scaffold370_size16199 mapping | 1407 | SNV | 1 | A | G | |
| MSH3 - Mismatch repair protein | scaffold378_size15716 mapping | 9884 | SNV | 1 | C | T | |
| grs1 - glutamine--tRNA ligase | scaffold3_size74209 mapping | 17748 | SNV | 1 | G | A | |
| rps3 - Ribosomal Protein | scaffold3_size74203 mapping | 52452 | SNV | 1 | T | C | |
| erf2 - Effect on Ras Function | scaffold400_size14210 mapping | 8380 | SNV | 1 | C | A | |
| IPO11 - Importin 11 | scaffold4458_size13240 mapping | 2983 | SNV | 1 | C | G | Ser210Cys |
| dak2 - Dihydroxyacetone Kinase | scaffold463_size13113 mapping | 4692 | SNV | 1 | C | A | Ser144Leu |
| LIP1_1 - Ceramide synthase subunit | scaffold471_size13041 mapping | 7493 | SNV | 1 | T | T | Asp42Gln |
| HST1 - Negatively affects Salt Tolerance | scaffold474_size12982 mapping | 7878 | SNV | 1 | A | C | |
| KIN4 - RNase | scaffold4_size73846 mapping | 72080 | SNV | 1 | G | G | Lys1488Glu |
| trs1 - similar to human TRRAP | scaffold502_size21960 mapping | 7426 | SNV | 1 | T | T | |
| COX17 - Cytochrome c Oxidase | scaffold502_size21960 mapping | 10968 | SNV | 1 | A | C | |
| APL4 - Gamma-adaptin | scaffold502_size21960 mapping | 11010 | SNV | 1 | A | T | |
| POL3_1 - POlymerase | scaffold51_size44861 mapping | 15667 | SNV | 1 | A | C | |
| HSP31 - Heat-Shock Protein | scaffold54_size43838 mapping | 86194 | SNV | 1 | A | C | Tyr53Asp |
| HIS3_1 - HIStidine | scaffold54_size43838 mapping | 28960 | SNV | 1 | G | T | |
| prp43 - Pre-mRNA Processing | scaffold57_size41873 mapping | 33520 | SNV | 2 | AG | A | Asn64Asn |
| | scaffold57_size41873 mapping | 51 | SNV | 2 | AG | C | |
| NTE1 - Serine esterase | scaffold598_size22109 mapping | 15248 | SNV | 1 | G | A | |
| avt3 - Amino acid Vacuolar Transport | scaffold598_size22109 mapping | 15674 | SNV | 1 | A | A | |
| sim2 - Serine/threonine-protein kinase | scaffold60_size10073 mapping | 2568 | SNV | 1 | T | A | |
| CWC27 - Complexed With Cef1p | scaffold60_size41194 mapping | 3458 | SNV | 1 | G | A | |
| Usp8 - Ubiquitin-specific peptidase | scaffold60_size41194 mapping | 13576 | SNV | 1 | A | A | |
| dfr1 - Dehydration responsive factor 1 | scaffold671_size90032 mapping | 1855 | SNV | 1 | A | G | |
| Bud3 - Budding Uninhibited by Benzimidazole | scaffold701_size85621 mapping | 6239 | MNV | 2 | AG | GT | |
| pho-4_3 - PHOsphate metabolism | scaffold737_size80219 mapping | 4410 | SNV | 1 | T | T | |
| cdon1 - CALLOSE DEFECTIVE MICROSPORE1 | scaffold73_size55071 mapping | 19198 | SNV | 1 | C | T | Ala35Val |
| rio1 - Right Open reading frame | scaffold74_size38522 mapping | 17358 | SNV | 1 | G | C | Glu143Lys |
| AGO2 - Argonaute 1 | scaffold752_size79762 mapping | 1326 | SNV | 1 | T | A | |
| VNX1 - Vacuolar Na+/H+ eXchanger | scaffold779_size78094 mapping | 1090 | SNV | 1 | G | C | |
| osms19 - Methyl Methanesulfonate sensitivity | scaffold780_size74437 mapping | 768 | SNV | 1 | C | A | Leu751Pro |
| KGD1 - alpha-Ketoglutarate Dehydrogenase | scaffold786_size36629 mapping | 2582 | SNV | 1 | T | A | Pro1161Leu |
| MMK1 - Mitogen-activated protein kinase kinase | scaffold878_size6181 mapping | 21994 | SNV | 1 | C | T | |
| | | 4015 | SNV | 1 | C | T | |
| rpc30 - RNA Polymerase C | scaffold918_size57348 mapping | 4030 | SNV | 1 | A | G | |
| | scaffold932_size56610 mapping | 4772 | SNV | 1 | G | A | |

OLEAGINOUS YEAST STRAIN AND USE THEREOF FOR THE PRODUCTION OF LIPIDS

CROSS-REFERENCE TO RELATED APPLICATIONS

The present application is a 35 U.S.C. § 371 National Stage patent application of International patent application PCT/IB2021/057746, filed on 24 Aug. 2021, which claims priority to Italian patent application 102020000020458, filed on 26 Aug. 2020, the contents of which are herein incorporated by reference in their entirety.

TECHNICAL FIELD

The present disclosure relates to a new oleaginous yeast strain of the species *Trichosporon oleaginosus*, characterized by mutations affecting the genome, which improve its thermotolerance.

The present disclosure also relates to a process for the production of lipids through the cultivation of said oleaginous yeast strain. The lipids thus obtained can be advantageously used as synthesis intermediates, particularly in the so-called "green chemistry" sector, or in the production of biofuels such as, for example, biodiesel or "green diesel", which can be used as they are, or in blends with other automotive fuels.

The microbiological production of lipids is proposed as an advantageous alternative to current production methods from renewable sources. Compared to the extraction of lipids from plants, microbiological processes are more convenient from an economic point of view because they are more easily scalable, require less manpower, and exploit the property of microorganisms to reproduce quickly at the expense of low-cost substrates such as, for example, derivatives from the hydrolysis of lignocellulosic materials. Furthermore, they are independent of climatic factors and do not compete with the agricultural exploitation of the soil for food use.

Oleaginous yeasts are particularly promising for this purpose, i.e. yeasts that are able, under specific cultivation conditions, to accumulate lipids, especially triglycerides, for over 25% of their dry weight.

BACKGROUND

The use of oleaginous yeasts for the production of lipids is part of the prior art as described, for example in:

Galafassi S. et al, *Bioresource Technol*. (2012), Vol. 111, pp. 398-403;

Capusoni C. et al, *Bioresource Technol*. (2017) 238: 281-289;

NogueVSI et al, *Green Chem,* 20 (2018), pp. 4349-4365;

Vasconcelos B. et al, *Appl Microbiol Biotechnol*. 2019 Mar. 25. doi: 10.1007/s00253-019-09742-x;

Spagnuolo M. et al, *Curr Opin Biotechnol*. 2019 Mar. 12; 57: 73-81. doi: 10.1016/j.copbio.2019.02.011.

Generally, said lipids are obtained through the cultivation of oleaginous yeasts under aerobic conditions in bioreactors. The oleaginous yeasts are grown using solutions of sugars that can be obtained from starchy plants or sugary fruits and are defined as "first generation sugars", or preferably are obtained by treatment and saccharification of non-edible lignocellulosic biomass, and are therefore defined as "sugars of second generation". Lignocellulosic biomasses can be, for example, agricultural residues such as wheat straw or corn stalks, or plants that cannot be used for the food sector such as common reed, fiber sorghum, miscanthus or processing residues of non-food plants such as guayule, eucalyptus, poplar, or forest residues or processing residues from the paper sector. These second-generation sugar mixtures, called hydrolysates, contain sugars with 5 (C5) and 6 (C6) carbon atoms. The oleaginous yeasts are naturally able to grow on C5 sugars such as xylose and C6 sugars such as glucose, producing cell biomass and, in particular growth conditions, accumulate lipids in high percentage compared to the dry cell weight.

From the cultivation of said oleaginous yeasts in the bioreactor, a culture broth is obtained including an oleaginous cell biomass that must be recovered. Subsequently, the lipids accumulated inside the cells must be extracted and separated from the culture broth still present and from the cellular debris resulting from the appropriate lysis or rupture techniques.

The technical solutions currently used for the microbiological production of lipids provide for the cultivation of these yeasts in bioreactors in processes that are carried out at controlled temperatures. As is known, each microbial species has an optimal growth temperature, which generally depends on the ecological environment in which the species lives in nature.

Since the fermentation processes of oleaginous yeasts are exothermic, very efficient cooling systems are required to maintain the optimal temperatures for microbial development, typically 20° C.-30° C., with a consequent increase in operating costs. Even a modest increase in the fermentation temperature (for example from 30° C. to 35° C.) therefore allows to obtain considerable advantages in terms of simplification of the cooling system and therefore of reduction of production costs.

Furthermore, if these fermentation processes are carried out using lignocellulosic wastes, which require enzymatic hydrolysis for the production of free monosaccharide mixtures (simultaneous saccharification and fermentation processes), the possibility of operating at higher temperatures is further advantageous in order to reduce the energy expenditure for maintaining the optimal temperatures of activity of the used hydrolytic enzymes (see for example Choudhary J. et al, *Electronic J. Biotechn* 2016; 21: 82-92).

The Applicant has therefore faced the problem of improving the thermotolerance of oleaginous yeasts suitable for the production of lipids, so as to allow to increase the fermentation temperature with respect to conventional processes and in any case guarantee the vital functions of the microorganism during the fermentation itself.

SUMMARY

The Applicant has found a new oleaginous yeast strain of the species *Trichosporon oleaginosus*, deposited on 28 May 2020 at Leibniz-Institut DSMZ, deposit number DSM 33530, which is able to perform its vital functions at higher temperatures than the strain parental, and therefore allows the use of higher fermentation temperatures, with consequent simplification of the cooling system of the bioreactor.

The new oleaginous yeast strain object of the present disclosure was obtained by mutagenesis of the oleaginous yeast strain of the species *Trichosporon oleaginosus* deposited on 17 May 2017 by the same Applicant at the Leibniz-Institut DSMZ, deposit number DSM 32508 (see also the patent application WO 2019/016703).

In a first aspect, the present disclosure therefore relates to the oleaginous yeast strain of the species *Trichosporon*

*oleaginosus*, deposited on May 28, 2020 at Leibniz-Institut DSMZ, deposit number DSM 33530.

In a second aspect, the present disclosure relates to a process for the production of lipids comprising:

preparing an inoculum comprising at least one oleaginous yeast strain of the species *Trichosporon oleaginosus* DSM 33530;

feeding said inoculum to a culture device obtaining a culture broth;

subjecting said culture broth to fermentation so as to obtain an oleaginous cell biomass comprising lipids in suspension in an aqueous phase;

separating the oleaginous cell biomass comprising lipids from the aqueous phase;

recovering the lipids present in the oleaginous cell biomass.

Thanks to the use of the strain object of the present disclosure, the fermentation phase can be carried out at relatively higher temperatures than known strains. The fermentation phase can generally be carried out at a temperature from 10° C. to 40° C., preferably from 30° C. to 40° C., even more preferably from 33° C. to 38° C.

In the present description and in the following claims, the definitions of the numerical ranges include the individual values within the range and its extremes, unless otherwise specified.

In the present description and in the following claims, the term "comprising" also includes the terms "which essentially consists of" or "which consists of".

In the present description and in the following claims, the term "biodiesel" refers to a fuel for diesel engines comprising alkyl esters (for example, methyl, propyl, or ethyl) of long-chain fatty acids deriving from biological sources.

In the present description and in the following claims, the term "green diesel" refers to a fuel for diesel engines comprising lipid hydrogenation or deoxygenation products deriving from biological sources in the presence of hydrogen and at least one catalyst.

In the present description and in the following claims, the expressions "cultivation" and "fermentation" indicate the processes through which the cells of a microorganism grow and reproduce under conditions controlled by human.

In the present description and in the following claims, the expression "culture medium" indicates a liquid, or a gel, designed to support the growth of microorganisms, in particular of oleaginous yeast cells. The culture medium can be of a defined composition (for example, "YPD" soil, "B" soil, etc.) or it can derive from the treatment of unselected sources such as, for example, waste water, commercial waste, or hydrolyzed lignocellulosic material.

In the present description and in the following claims, the expressions "carbon source", "nitrogen source", "sulfur source" and "phosphorus source" mean organic or inorganic substances, or compositions of said substances respectively based on carbon, nitrogen, sulfur (for example sulphates) and phosphorus (for example phosphates), contained in the culture medium and which a microorganism can metabolize to derive energy.

In the present description and in the following claims, the term "biomass" refers to the set of cells produced during the process for the production of lipids object of the present disclosure or in other culture methods.

BRIEF DESCRIPTION OF THE DRAWINGS

To better understand the characteristics of the present disclosure, reference will be made to the following figures in the description:

FIG. 1, which includes Table 1 and shows the mutations detected in the genomic DNA of the new strain DSM 33530 compared to the parental strain DSM 32508 according to the disclosure;

FIG. 2, which includes Table 2 and shows the mutations detected in the genomic DNA of the new strain DSM 33530 compared to the parental strain DSM 32508 according to the disclosure;

DETAILED DESCRIPTION OF THE DISCLOSURE

Figure 3:
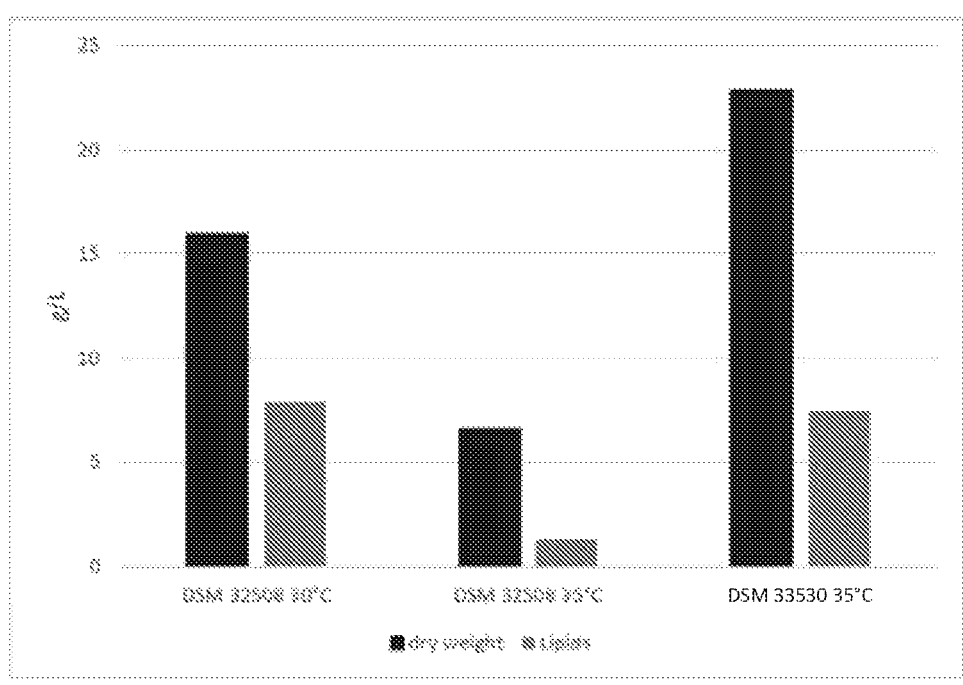
FIG. 3, which includes a graph showing the biomass and lipid production of the new strain DSM 33530 compared with the parental strain DSM 32508 according to the disclosure.

Further features and advantages of the present disclosure will become apparent from the following detailed description.

The oleaginous yeast strain object of the present disclosure was obtained by mutagenesis of the strain of the species *Trichosporon oleaginosus* DSM 32508, described in patent application WO 2019/016703, and subsequent selection of the mutants characterized by a greater thermotolerance.

More in detail, the mutagenesis process was carried out through the exposure of cells of the parental strain DSM 32508 to ultraviolet (UV) radiation with a wavelength ranging from 230 nm to 260 nm. Mutagenesis by exposure to UV radiation can be carried out according to the known art as described, for example, in Winston F. et al, *Current Protocols in Molecular Biology* (2008), John Wiley & Sons; DOI: 10.1002/0471142727.mb1302s82. For example, said mutagenesis can be achieved by exposing the cells of the parental strain deposited in a Petri dish on solidified medium with agar to a source of UV radiation, placed at a distance from the Petri dish ranging from 10 cm to 50 cm, for a time ranging from 5 seconds to 5 minutes. The UV radiation source is generally one or more lamps with power ranging from 8 Watts to 15 Watts, which generate radiation with a wavelength ranging from 230 nm to 260 nm.

The change in the cell morphology of the oleaginous yeast strain of the species *Trichosporon oleaginosus* DSM 33530, compared with the parental strain DSM 32508, was verified in several experiments, some of which described in the examples below, in which said modification was detected both under the optical microscope, and by flow cytofluorimetry.

The genotype of the strain DSM 33530 object of the present disclosure was also characterized by analyzing the sequence of its entire genomic DNA and comparing the results with those of its parental strain DSM 32508 with bioinformatics tools. The details are reported in Example 2.

Tables 1 and 2 attached to this description (as FIG. 1 and FIG. 2) report the mutations detected in the genomic DNA of the new strain DSM 33530 compared to the parental strain DSM 32508. For each mutation, the position on the so-called "scaffold" is indicated, i.e. on one of the contiguous regions of genomic DNA which, assembled on the basis of their nucleotide sequence, allow the reconstruction of the genome. The types of mutation (SNV: "single nucleotide variation", i.e. mutation of a single nucleotide; MNV: "multiple nucleotide variation", i.e. mutation of several nucleotides in sequence; Insertion of one or more nucleotides; Deletion of one or more nucleotides); the number of nucleotides involved, the amino acid mutated in the genome of the parental strain DSM 32508 and in the genome of the strain DSM 33530, respectively, are also indicated. Mutations in homozygosity are those found in genes present in single copy in the genome (Table 1); mutations in heterozygosity are those found in genes present in multiple copies in the genome (Table 2). The genes whose mutations can have a direct or indirect effect on the improved thermotolerance of the strain DSM 33530 are indicated in bold.

Determining the precise effect of a mutation is currently very difficult, as it would be necessary to produce a knock-out mutant for each mutated gene. Currently there are no molecular tools for this yeast species that allow this to be done.

Complex mutations, such as deletions and insertions, but also single nucleotide mutations (SNVs) can destroy/damage a gene or have a positive impact, improving its stability or promoting its transcription. The same is true for the protein encoded by the mutated gene; this may be inactive or may show greater activity/stability.

Thermotolerance is a complex phenotype, made possible thanks to the activation of numerous mechanisms including those concerning the permeability of the cell membrane, the denaturation of proteins, as well as the regulation of enzymes that repair damage on DNA and RNA. In fact, it is probable that the ability to grow at higher temperatures is not determined by a specific mutation in a gene but results because of a series of homozygous and heterozygous mutations in several points of the genome, which together determine the thermotolerant phenotype of the new oleaginous yeast strain of the species *Trichosporon oleaginosus* DSM 33530.

The precise number and nature of genes involved in the acquisition of thermotolerance can vary greatly between organisms; however, at the level of molecular "chaperones", the response is conserved (Richter K. et al, *Mol. Cell,* 2010, Volume 40, Issue 2, p. 253-266). In fact, Table 1 highlights the mutation in the gene encoding HSP104p, a highly conserved protein among living organisms of the 'Heat Shock Protein' (HSP) family. These proteins are strongly related to thermotolerance, their expression in fact induced by stress conditions such as thermal shock and exposure to UV light (Lindquist and Craig (1988) *The Heat-shock proteins. Annual Review of Genetics*, Vol. 22, p. 631-677). HSP104p is located in the cytosol where it acts as a molecular chaperone; in fact, its thermoprotective function consists in repairing heat-damaged proteins and making aggregates of unfolded polypeptide chains soluble (Parsell D. A. et al (1994) *Nature,* 372 (6505), p. 475-8).

It has been shown how HSP104p acts together with other molecular "chaperones" to solve and prevent the misfolding and aggregation of proteins, phenomena favored during growth at high temperatures. The molecular mechanisms by which molecular "chaperones" modulate the aggregation, disaggregation and clearance of protein aggregates remain today the subject of debate and intense investigation (Grimminger Marquardt V. et al (2009) *Biopolymers*, Volume 93, Issue 3, p. 252-276).

In the case in question, a single homozygous mutation in the HSP104 gene causes the substitution of an amino acid, from an uncharged polar one (Asn) to a positively charged one (His). This can change the stability of the protein and/or the type of interaction with other chaperones.

The acquisition of thermotolerance in the strain new DSM 33530 can also be favored by mutations in homozygosity (Table 1) that fall into genes involved in the ubiquitin mechanism (uba3, HSE1), in the regulation of apoptosis (Wdr), in intracellular trafficking (snx12) and in DNA damage repair (REV1) (Larimer F. W. et al (1988) *Journal of bacteriology, vol* 171, p. 230-237).

Table 2 lists the mutations present in heterozygosity, therefore on only one allele of the mutated gene. Genes highlighted in bold are correlated, albeit indirectly, to high temperature tolerance; genes coding for proteins related to chromatin silencing (HST3), to repair of double-stranded DNA breaks (RAD), to maintenance of the mitochondrial genome (COX18) are mutated (Jarolim S. et al (2013) G3 (Bethesda), 9; 3(12), p. 2321-33).

Although heterozygous, all these mutations associated with homozygous mutations could cause profound alterations in the response to heat stress and therefore be related to the phenotype of the new strain DSM 33530 of different temperature tolerance.

Furthermore, some mutations found in the new strain DSM 33530 are not related to the acquisition of thermotolerance but to the accumulation of lipids. In other species of oleaginous yeasts, the correlation between mutations in genes for auxotrophy (METS, ARG2, HIS3) and the increase in lipid production has been highlighted (Coradetti S. T. et al (2018), eLife 2018; 7:e32110).

As already reported, the present disclosure also relates to a process for the lipid production comprising:

preparing an inoculum comprising at least one oleaginous yeast strain of the species *Trichosporon oleaginosus* DSM 33530;

feeding said inoculum to a culture device obtaining a culture broth;

subjecting said culture broth to fermentation so as to obtain an oleaginous cell biomass comprising lipids in suspension in an aqueous phase;

separating the oleaginous cell biomass comprising lipids from the aqueous phase;

recovering the lipids present in the oleaginous cell biomass.

The culture device can be, for example, a bioreactor. The separation phase can be carried out, for example, by centrifugation.

Preferably, the fermentation phase can be carried out at a temperature from 10° C. to 40° C., preferably from 30° C. to 40° C., even more preferably from 33° C. to 38° C.

Preferably, the fermentation phase can be carried out for a time ranging from 40 hours to 200 hours, preferably ranging from 80 hours to 150 hours.

Preferably, the fermentation phase can be carried out under aerobic conditions. Said aerobic conditions can be implemented, for example, by blowing sterile air into the culture device and by agitation, said agitation depending on the type of used culture device.

Preferably, the dissolved oxygen concentration ($DO_2$, Dissolved Oxygen) is maintained at 20%-40% of the saturation value during the fermentation phase.

Furthermore, the fermentation phase can be carried out in a bioreactor containing a fermentation medium comprising glucose, ammonium phosphate, YE (yeast extract), CSS, $KH_2PO_4$, $MgSO_4$, $CaCl_2$), NaCl, and any inhibitors of the fermentation process, such as for example acetic acid. This fermentation medium preferably has a concentration of 400 mL/L.

Furthermore, it is optionally possible to feed the culture with a nitrogen flow in order to restore the initial concentrations of YE and ammonium sulphate.

Preferably, during the fermentation phase, the culture is fed with glucose in order to keep the sugar concentration greater than zero throughout the process.

In accordance with a preferred embodiment of the present disclosure, the fermentation phase can be carried out at a pH ranging from 3.0 to 8.0, preferably ranging from 4.0 to 7.0. In order to maintain the pH in the desired ranges, it can be added to the culture medium an aqueous solution of at least one inorganic base such as, for example, sodium hydroxide (NaOH), potassium hydroxide (KOH), calcium dihydroxide [Ca(OH)$_2$], magnesium hydroxide [Mg(OH)$_2$], or mixtures thereof, preferably potassium hydroxide (KOH), or an aqueous solution of at least one inorganic acid such as, for example, phosphoric acid (H$_3$PO$_4$), sulfuric acid (H$_2$SO$_4$), hydrochloric acid (HCl), or mixtures thereof, preferably sulfuric acid (H$_2$SO$_4$), in such quantity as to obtain the desired pH.

Preferably, the fermentation phase can be carried out starting from an inoculum in a quantity ranging from 1% to 5% (vol/vol) of the total volume of culture medium, obtained from a previous culture of said strain DSM 33530, carried out in the same culture medium for a time ranging from 6 hours to 24 hours.

Said previous culture can in turn be inoculated from an anterior culture, or it can be inoculated starting from a sample of the strain DSM 33530, kept at −80° C. in suspension containing 15% (vol/vol) glycerol.

Preferably, the fermentation phase can be carried out in a culture medium comprising glucose as a source of carbon and ammonium sulfate [(NH$_4$)$_2$SO$_4$] as a source of nitrogen.

In accordance with a preferred embodiment of the present disclosure, the fermentation phase can be carried out in discontinuous culture ("fed-batch").

Preferably, the fermentation phase, after a time ranging from 15 hours to 25 hours after inoculation, can be further carried out in "fed-batch", preferably for a time ranging from 25 hours to 175 hours, more preferably ranging from 65 hours to 125 hours, adding at least one additional source of nitrogen such as, for example, "corn steep liquor" or "corn steep solid", yeast extract, ammonium sulphate, urea, in such quantities as to add to the culture broth an amount total of nitrogen ranging from 0.5 g/L to 5 g/L.

Preferably, after a time ranging from 15 hours to 25 hours after inoculation, the fermentation phase can be further carried out in "fed-batch", preferably for a time ranging from 25 hours to 175 hours, more preferably ranging from 65 hours to 125 hours, adding an aqueous solution of glucose so as to have a constant concentration of glucose in the culture broth ranging from 25 g/L to 50 g/L.

Cell growth during culture can be measured by spectrophotometric methods by determining the turbidity, or optical density (OD) of a sample of culture broth at 660 nm (OD660).

At the end of the fermentation phase, the cells of the strain DSM 33530 can be separated from the culture broth by methods known in the art such as, for example, filtration, filterpressing, microfiltration or ultrafiltration, centrifugation, preferably by centrifugation. Preferably, said centrifugation can be carried out for a time ranging from 5 minutes to 30 minutes, preferably ranging from 15 minutes to 25 minutes, at a rotation speed ranging from 3000 rpm to 9000 rpm, preferably ranging from 4000 rpm to 8000 rpm. It should be noted that the operating conditions indicated for centrifugation relate to a process carried out on a laboratory scale: in the case of an industrial process, in which continuous centrifuges are generally used, the skilled in the art will be able to adapt these operating conditions.

The concentration of the obtained oleaginous cell biomass can be measured in grams per liter of culture broth, by determining the dry weight of the oleaginous yeast cells of a sample of culture broth of known volume taken at predetermined intervals and at the end of said process. In particular, by "dry weight" of the oleaginous cell biomass we mean the weight of the cells contained in a known volume of culture broth, determined by weighing the aforementioned cells after having eliminated all the water content through a heat treatment in a ventilated oven at 105° C. up to constant weight (about 24 hours).

The oleaginous cell biomass of the recovering phase of the lipids can be subjected to cell lysis according to processes known in the art and described, for example, in the international patent application WO 2014/102254 including, for example, heat treatment in a pressurized reactor, mechanical treatment with homogenizer, or treatment with microwaves.

At the end of said cell lysis, the lipids can be recovered from the obtained suspension, by extraction with polar or apolar organic solvents, according to processes known in the art and described, for example, in the international patent application WO 2014/102254.

The production of lipids by oleaginous yeasts at the end of the process object of the present disclosure can be measured with colorimetric methods known in the art, directly in samples of yeast cell suspensions, for example with sulfo-phospho-vanillin using, for example, the kit "Total lipids-sulfo-phospho-vanillin" marketed by Spinreact S. A. U., Ctra. Santa Coloma, 7 E-17176 St. Esteve d'en Bas (GI), Spain.

Furthermore, the amount of lipids produced can be determined by gravimetric methods on the fraction extracted with mixtures of organic solvents, for example with chloroform: methanol 2:1, vol/vol as described in Folch J. et al, *The Journal of Biological Chemistry* (1957), vol. 226, p. 497-509; or extracted with n-hexane:isopropanol 3:2 vol/vol as described in Hara A. et al, *Analytical Biochemistry* (1978), Vol. 90, p. 420-426, from lyophilized biomass samples.

Consequently, to evaluate the performance concerning the accumulation of lipids in the strain DSM 33530 compared to the parental strain DSM 32508, the dry weight of the biomass (expressed in g/L) and the quantity of lipids (expressed in g/L) were determined with the methods listed above at the end of the process and the percentage ratio was calculated between these two parameters.

The lipid fraction was analyzed by chromatographic techniques, for example by gas chromatography or by high performance liquid chromatography (HPLC) according to processes of the known art.

Through said analytical methods it was found that the lipids accumulated in the oleaginous yeast cells, both of the strain DSM 33530 object of the present disclosure and of the parental strain DSM 32508, are represented for 90% by triglycerides, preferably esters of glycerol with fatty acids having from 8 to 24 carbon atoms, such as, for example, palmitic acid, stearic acid, oleic acid and α-linoleic acid.

Other lipids that may be present are: phospholipids, monoglycerides, diglycerides, free fatty acids, or mixtures thereof.

The lipids obtained according to the process object of the present disclosure can be advantageously used as synthesis intermediates, particularly in the so-called "green-chemistry" sector. Furthermore, they can be subjected to transesterification in the presence of at least one alcohol having from 1 to 4 carbon atoms, preferably methanol or ethanol, and of at least one acid or basic catalyst, in order to produce glycerol and alkyl esters, in particular methyl esters or ethyl esters (biodiesel).

Alternatively, said lipids can be subjected to hydrogenation/deoxygenation in the presence of hydrogen and at least one catalyst in order to produce "green diesel". Hydrogenation/deoxygenation processes are known in the art and are described, for example, in the European patent application EP 1,728,844.

In order to further illustrate the present disclosure, some examples of embodiment are reported below, which must not be interpreted in a limiting sense of the scope of the disclosure itself.

Example 1: Obtaining and Selection of the Oleaginous Yeast Strain of the Species *Trichosporon oleaginosus* DSM 33530

A sample of cells from the parenteral strain of oleaginous yeast of the species *Trichosporon oleaginosus* DSM 32508 was inoculated into a flask containing "YPD" medium (yeast extract 10 g/L, peptone 20 g/L, glucose 20 g/L): the flask was placed in a shaking incubator, at 30° C., overnight. The cells were then separated and collected by centrifugation at 3,500 rpm for 5 minutes, washed in sterile water, then diluted and plated on Petri dishes containing "YPD" medium in order to have about 100 colonies.

The plates were exposed to a source of ultraviolet radiation, represented by a 15 Watt UV lamp (wavelength 254 nm), placed at a distance of 15 cm, for a time equal to 40 seconds, in order to obtain a rate residual viability of 10%. Thereafter, the plates were incubated at 35° C. for 4 days until the colonies reached sufficient size to be counted.

After mutagenesis, colonies of the *Trichosporon oleaginosus* species capable of growing at 35° C. were selected as follows.

Among the pool of mutants obtained at 35° C., a certain number of colonies that reached larger sizes were incubated in liquid "YPD" medium (yeast extract 10 g/L, peptone 20 g/L, glucose 20 g/L) and a first selection was made based on the growth rate at 35° C. Cell growth was evaluated by spectrophotometric method by determining the optical density of a sample of culture broth at 660 nm ($OD_{660}$). These cultures were used to prepare suspensions containing 15% (vol/vol) glycerol maintained at −80° C. for the storage of the obtained mutants of oleaginous yeast of the *Trichosporon oleaginosus* specie.

The mutant of oleaginous yeast of the species *Trichosporon oleaginosus* which showed the best kinetics growth was incubated at 35° C. in lipidogenic medium 'B' (glucose 50 g/L, ammonium sulfate [$(NH_4)_2SO_4$] 1 g/L, yeast extract 1 g/L, potassium dihydrogen phosphate [$KH_2PO_4$] 1 g/L, magnesium sulfate heptahydrate [$MgSO_4·7H_2O$] 0.05 g/L, sodium chloride [NaCl] 0.01 g/L, calcium chloride dihydrate [$CaCl_2·2H_2O$] 0.01 g/L) to monitor lipid production. For comparative purposes, a sample of the parental strain DSM 32508 was incubated under the same conditions at 35° C.

To evaluate the lipid accumulation of the new strain DSM 33530 compared to the parental strain DSM 32508, the dry weight of the biomass (expressed in g/L) and the quantity of lipids (expressed in g/L) were determined and the percentage ratio between these two parameters was calculated.

The production of lipids by oleaginous yeasts can be measured with colorimetric methods known in the art, directly in samples of yeast cell suspensions, for example with sulfo-phospho-vanillin using, for example, the "Total lipids-sulfo-phospho-vanillin" kit marketed by Spinreact SAU, Ctra. Santa Coloma, 7 E-17176 St. Esteve d'en Bas (GI), Spain.

FIG. 3 shows the biomass (dry weight) and lipid production (expressed in g/L) of the new strain DSM 33530 incubated at 35° C., compared with the parental strain DSM 32508 incubated at 30° C. and 35° C., after 96 hours of incubation.

Figure 4:
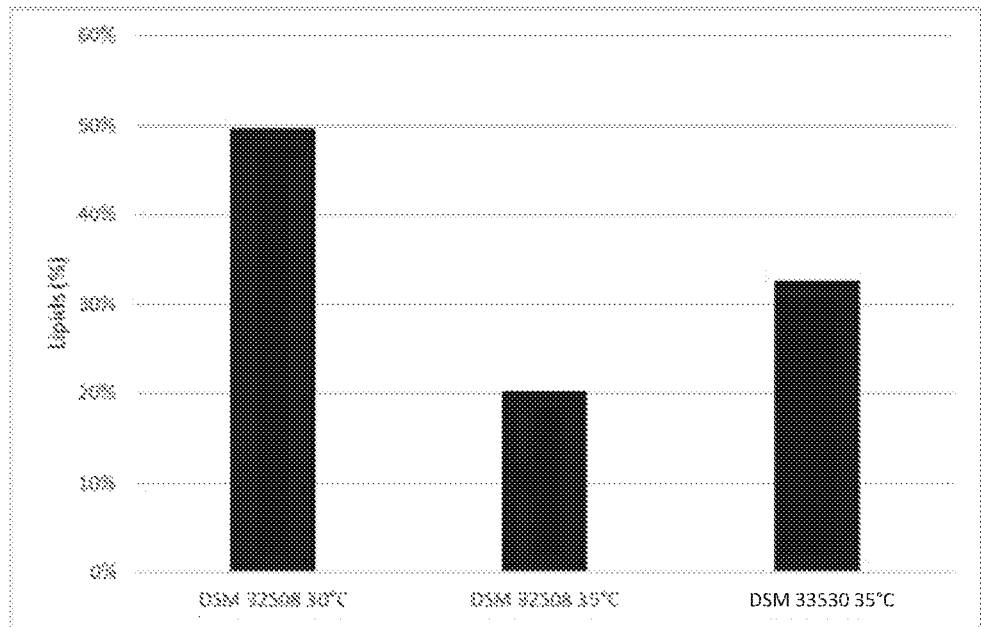
FIG. 4, which includes a graph showing the lipid production of the mutant DSM 33530 compared with the parental strain DSM 32508 according to the disclosure.

FIG. 4 reports the lipid production, expressed as % dry weight, of the mutant DSM 33530 incubated at 35° C. in comparison with the parental strain DSM 32508 incubated at 30° C. and 35° C., after 96 hours of incubation.

The mutant DSM 33530 has been shown to have a higher lipid production than the parental strain DSM 32508 grown at 35° C., both in terms of concentration (g/l) and in terms of dry weight. Comparing the new mutant with the performance of the parental strain at its optimal temperature, it is observed that the new microorganism reaches the same lipid titer (7.5 g/l) and a greater quantity of microbial biomass.

Example 2: Genotypic Characterization of the Oleaginous Yeast Strain of the Species *Trichosporon oleaginosus* DSM 33530

The genotypic characterization of the strain DSM 33530 reported in Tables 1 and 2 already illustrated above was obtained as follows.

The genotype of the oleaginous yeast strain of the species *Trichosporon oleaginosus* DSM 33530 was characterized by analyzing the sequence of its entire genomic DNA and comparing the results with those of its parental oleaginous yeast strain of the species *Trichosporon oleaginosus* DSM 32508 using bioinformatics tools.

For this purpose, genomic DNA was extracted from cultures of both strains made in "YPD" medium (yeast extract 10 g/L, peptone 20 g/L, glucose 20 g/L) overnight. The extracted DNA was purified with Quiagen's commercial DNeasy Blood & Tissue kit (cat. No. 69504) following the manufacturer's instructions.

After verification of the degree of purity and integrity by electrophoresis, the genomic DNA of each strain was separately treated with the commercial kit "TrySeq DNA Library Preparation Kit" from Illumina following the protocol combined with the kit. In short, the DNA was processed in order to obtain fragments with dimensions ranging from 200 to 400 base pairs, then, ligated at the 3' and 5' ends to oligonucleotide adapters supplied in the kit and subsequently amplified by means of a polymerase chain reaction (PCR) using the same oligonucleotides as "primer". Gene amplification products were quantified and checked with Agilent Technology's Bioanalyzer 2100 instrument. The DNA sequence of each fragment obtained was determined using Illumina sequencer "HiSeqR® 2500 Sequencing Systems" and the sequences obtained were optimized based on the "phred" value as described, for example, in Ewing B. et al., *Genome Research* (1998), Vol. 8(3), p. 175-185.

Sequence analysis allowed the identification of 1703 contiguous regions ("contig") with an average size of 11605 base pairs (contig with a minimum length of 300 base pairs were considered), for a total of 19,763,953 base pairs. This value is in line with the size of the genomic DNA of yeasts phylogenetically similar to the genus *Trichosporon*, therefore it is believed that the resulting libraries represent the complete genome of the strain DSM 33530 and the parental strain DSM 32508. The sequences of the two genomic DNAs were compared using CLCbio software "Map Reads to Reference" and "Quality-based Variant Detection".

The identified mutations were confirmed by verifying their existence in both sequencing directions and determining their accuracy through the "phred" value.

The genome of the parental strain DSM 32508 has a size of 19,800,719 bp and contains 7,786 genes of which 3,995 have been identified with a known function. Comparison with the DSM 33530 genome revealed a total of 889 mutations, including 61 deletions, 40 insertions, 727 variations of a single nucleotide (SNV) and 61 variations of more than one nucleotide (MNV). Of all the mutations identified, 568 are heterozygous (found in one allele only) and 321 are homozogotic (found in both alleles of the mutated gene).

Example 3: Fermentation Process in a Bioreactor for the Production of Lipids

The growth and accumulation of lipids of cells of the parental strain DSM 32508 and of cells of the strain DSM 33530 according to the disclosure were evaluated.

For this purpose, a sample of cells of the strain DSM 33530 and a sample of cells of the parental strain DSM 32508 were inoculated, in two 500 mL flasks, in 100 mL of "YPD" medium (yeast extract 10 g/L, peptone 20 g/L, glucose 20 g/L): the flasks were placed in a shaken incubator overnight, respectively 35° C.

The cell suspensions thus obtained were used to inoculate 1 L bioreactors, containing 400 ml of medium as follows: glucose 50 g/L, $(NH_4)_2SO_4$ 5 g/l, YE 2 g/l, CSS 5 g/l, $KH_2PO_4$ 6 g/l, $MgSO_4·7H_2O$ 0.3 g/l, $CaCl_2·2H_2O$ 0.06 g/l, NaCl 0.06 g/l.

The fermentation processes were carried out under the same conditions at a temperature of 35° C.

The volume of inoculation for each strain is that necessary to obtain 400 mL of suspension having a cell concentration of 0.5 $OD_{660}$.

Growth took place under aerobic conditions by insufflation of air at 1 L/min and agitation variable between 250 and 1050 rpm according to the strain's needs in order to maintain the dissolved oxygen concentration ($DO_2$, Dissolved Oxygen) equal to 30% of the saturation value. The pH was maintained at about 5.0 by adding, when necessary, a solution of KOH 5 M.

The fermentation process was carried out in "fed-batch" way for 93 hours. After 24 hours, the culture was fed with a nitrogen "feed" in order to restore the initial concentrations of yeast extract and ammonium sulphate. In order to keep the sugar concentration greater than zero constant throughout the process, a sugar feed was carried out with a 600 g/L glucose solution, carried out at a variable speed between 2 and 10 g/h until the end of the process.

Table 3 shows the results obtained in terms of productivity of the two processes.

TABLE 3

|  | DSM 32508 | DSM 33530 |
| --- | --- | --- |
| hours (h) | 93 | 93 |
| X (g/L) | 10 | 80.73 |
| lipids (g/L) | — | 44.55 |

TABLE 3-continued

|  | DSM 32508 | DSM 33530 |
| --- | --- | --- |
| lipids % (w/w) | — | 55.19 |
| Y x/s | 0.20 | 0.26 |
| Y L/s (g/g) | — | 0.14 |
| P (g/L/h) | — | 0.48 |

The amount of biomass (X) is expressed as the weight of dry biomass per liter of culture. The quantity of lipids produced is expressed both as grams of lipids per liter of culture, and as a percentage ratio with respect to the dry biomass X.

Y x/s represents the quantity of biomass (in grams) produced per gram of sugar consumed; Y L/s is instead the quantity of lipids (in grams) produced per gram of sugar consumed. P g/L/h is instead the quantity of lipids produced (g/L) per hour.

Figure 5:
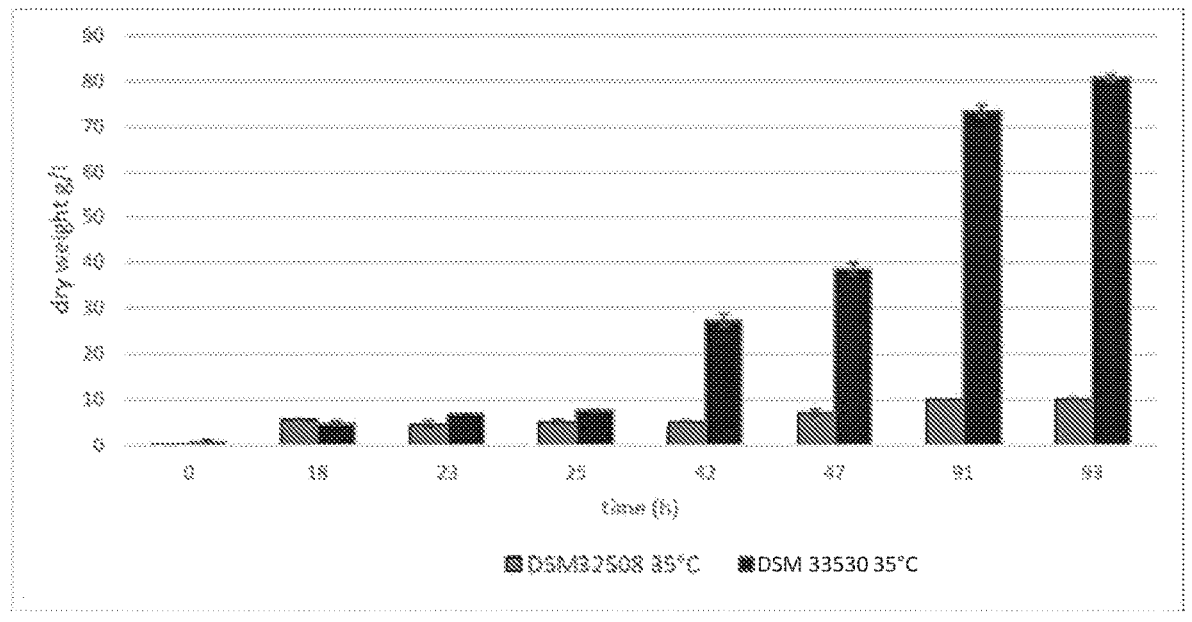
FIG. 5, which includes a graph showing the biomass production of the new strain DSM 33530 compared with the parental strain DSM 32508 according to the disclosure.

FIG. 5 shows the biomass production (expressed as g/L on dry matter) at 35° C. of the new strain DSM 33530 compared with the parental strain DSM 32508. The significant difference in terms of productivity between the two strains is evident. For the parental strain, the lipid concentration values are below the detection limit of the technique used, so the corresponding yield (Y l/s) and productivity (P) values are not reported either.

The invention claimed is:

1. The oleaginous yeast strain of the species *Trichosporon oleaginosus*, deposited on 28 May 2020 at Leibniz-Institut DSMZ, deposit number DSM 33530.

2. A process for lipid production including the following steps:
   preparing an inoculum comprising the oleaginous yeast strain of the species *Trichosporon oleaginosus* DSM 33530,
   feeding said inoculum to a culture device obtaining a culture broth,
   subjecting said culture broth to fermentation so as to obtain an oleaginous cell biomass comprising lipids in suspension in an aqueous phase,
   separating the oleaginous cell biomass comprising lipids from the aqueous phase, and
   recovering the lipids present in the oleaginous cell biomass.

3. The process according to claim 2, wherein the fermentation is carried out at a temperature from 10° C. to 40° C.

4. The process according to claim 2, wherein the fermentation is carried out for a time ranging from 40 hours to 200 hours.

5. The process according to claim 2, wherein the fermentation is carried out in aerobic conditions.

6. The process according to claim 5, wherein during the fermentation, the dissolved oxygen concentration ($DO_2$, Dissolved Oxygen) is maintained at 20%-40% of the saturation value.

7. The process according to claim 2, wherein the fermentation is carried out at a pH ranging from 3.0 to 8.0.

8. The process according to claim 2, wherein the fermentation is carried out in a culture medium comprising glucose as source of carbon and ammonium sulfate [$(NH_4)_2SO_4$] as source of nitrogen.

9. The process according to claim 2, wherein the fermentation is carried out in a discontinuous culture.

* * * * *